United States Patent
O'Hara

(10) Patent No.: US 6,442,231 B1
(45) Date of Patent: Aug. 27, 2002

(54) APPARATUS AND METHOD FOR IMPROVED ENERGY DISPERSIVE X-RAY SPECTROMETER

(76) Inventor: David B. O'Hara, 4356 David Ct., Tallahassee, FL (US) 32308

( * ) Notice: Subject to any disclaimer, the term of this patent is extended or adjusted under 35 U.S.C. 154(b) by 0 days.

(21) Appl. No.: 09/485,526
(22) PCT Filed: Aug. 14, 1998
(86) PCT No.: PCT/US98/16907
§ 371 (c)(1), (2), (4) Date: Feb. 10, 2000
(87) PCT Pub. No.: WO99/09401
PCT Pub. Date: Feb. 25, 1999

Related U.S. Application Data
(60) Provisional application No. 60/055,829, filed on Aug. 15, 1997.

(51) Int. Cl.⁷ .............................................. G01N 23/223
(52) U.S. Cl. ............................. 378/45; 378/84; 378/145
(58) Field of Search ................................ 378/45–49, 84, 378/85, 145

(56) References Cited

U.S. PATENT DOCUMENTS
3,143,651 A * 8/1964 Giacconi ...................... 378/43
5,497,008 A * 3/1996 Kumakhov ............... 250/505.1

* cited by examiner

Primary Examiner—Craig E. Church
(74) Attorney, Agent, or Firm—Allen, Dyer, Doppelt, Milbrath & Gilchrist, P.A.

(57) ABSTRACT

The invention is an improved energy dispersive x-ray spectrometer comprising x-ray source (10), sample (12), optics (20) and detector (16). The improvement comprises the use of optics using the principle of total external reflection for delivering an increased flux of x-rays onto the detector. These flux concentrating optics are generally shaped as tubes having a figure of revolution as a longitudinal cross section such as a cone, parabola, hyperbola, ellipsoid and others. These optics may also be used as low energy pass filters by incorporating a stop (22) at or near the aperture of the optic. The reflecting surface of the flux concentrator optic may be selected from the group of metals and their alloys, the choice made to optimize the optic's performance.

35 Claims, 3 Drawing Sheets

APPARATUS AND METHOD FOR IMPROVED ENERGY DISPERSIVE X-RAY SPECTROMETER

This application claims benefit of provisional application 60/055,829 filed Aug. 15, 1997.

BACKGROUND

1. Field of Invention

This invention relates to the field of x-ray spectrometry and other instrumentation relying on energy dispersive spectrometry analysis of x-rays emitted from a target, and specifically to a method and apparatus for preserving the flux of x-rays emitted from said target and available for analytical purposes within the instrument.

2. Description of Prior Art

In x-ray spectroscopic elemental analyses, there are two main techniques for separating into their various energies the x-rays emitted from the sample under analysis, these are wavelength dispersive spectroscopy (WDS) and energy dispersive spectroscopy (EDS).

WDS uses Bragg reflection from a crystal to separate the x-rays into various wavelengths, while EDS uses a solid state device whose output is a known function of the x-ray energy to separate them into various energy bins. For reasons of mechanical simplicity, data collection times, spectrometer size and various other technical reasons, EDS is frequently preferred over WDS. Unfortunately, EDS systems are frequently inefficient at detection of very low energy x-rays and this inefficiency is exacerbated by the low production rate of low energy x-rays compared to higher energy ones. These low energy x-rays correspond to those emitted by light elements such as Be, B, C, N, O, and F and also the so-called L lines of the heavier elements. Because of the low production rate of these low energy x-rays compared to higher energy ones, an EDS system spends most of its time counting pulses from higher energy x-rays, thus adversely affecting the instrument's detection limit for the light elements, thereby making these elements detectable by EDS only when found in relatively high concentration in the sample. The x-ray lines for the light elements are closer in energy than those for the heavier elements and many EDS systems have difficulty resolving these x-ray lines when L lines from heavier elements are also emitted by the sample. EDS cannot be used for light element analyses except in special cases or if the EDS detector is specially configured for optimum resolution. Resolution is often a decreasing function of detector size, because a smaller detector has less capacitance than a larger one. Also, a small detector subtends a smaller collection angle than a larger one, resulting in a lower count rate. In some cases, the size of the detector is limited by the instrument's geometry, so that a smaller detector is necessary even when poor resolution occurs. For example, some electron microscopes have sufficiently close working distances or otherwise poor access to x-rays emitted from a sample, that either a very small detector must be used or the detector must be placed far from the x-ray source.

OBJECTS AND ADVANTAGES

Accordingly, several objects and advantages of the present invention are:

a) to solve the practical problem of increasing the efficiency of x-ray detection in an energy dispersive x-ray spectrometer by gathering x-rays that are diverging away and redirecting them through an aperture;

b) to provide an energy dispersive x-ray spectrometer which collects data faster than existing systems;

c) to provide an energy dispersive x-ray spectrometer which is more sensitive than previous instruments, d) to teach a method to limit the area of the target from which x-rays reach the detector, thereby allowing the analysis of very small areas within a sample.

LIST OF REFERENCE NUMERALS

Figure 1:
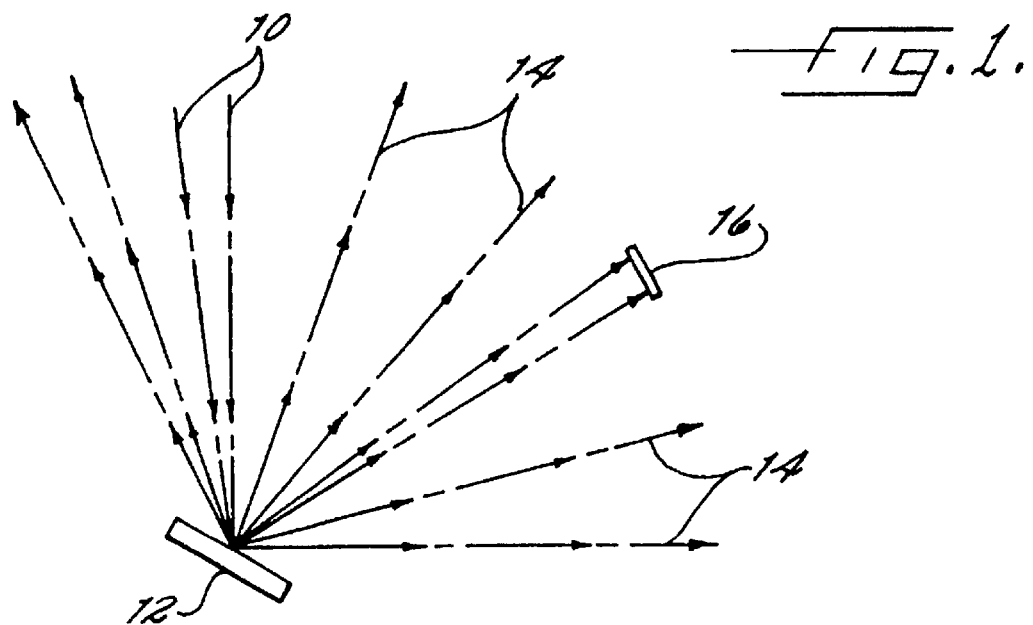
FIG. 1. shows an X-Ray source with x-rays being emitted into a large solid angle, some of them reaching the detector.

Incident energy beam
12 Target sample
14 Emitted isotropic x-rays
16 Detector
18 Redirected x-rays
20 Optic
22 Aperture stop
24 Entrance aperture
26 Exit aperture
28 Paraboloid focus

SUMMARY

This invention teaches a method and apparatus for directing a larger flux of x-rays onto the x-ray detector in an energy dispersive spectrometer, thereby allowing the detector to see more x-rays. By providing for a larger stream of x-rays falling onto the detector, this invention allows faster data collection and, thereby, greater sensitivity in the instrument. In addition, by teaching a method and apparatus allowing the selective isolation of x-rays emitted from very small areas of a source sample, the invention allows the analytical differentiation and localization of elements within a composite sample.

DESCRIPTION OF THE INVENTION

The invention disclosed in this patent application concerns a method of improving an energy dispersive x-ray spectrometer (EDS) through the use of a reflecting optic 20 by collecting through an entrance aperture 24 the isotropic x-rays 14 emitted from the target sample 12 and guiding those redirected x-rays 18 through an exit aperture 26 onto the x-ray detector 16. The optics 20 herein described, when fitted with a stop 22 at or near the entrance aperture 24, may also be used in the EDS as low-pass filters that reduce the number of higher energy x-rays reaching the detector 16 and may be used as well to spatially define the area of the target sample 12 from which emitted x-rays 14 are selected for analysis.

The optics 20 described in this application are specifically of the type known as "grazing incidence optics", which use the principle of total external reflection for the efficient collection of x-rays. Grazing incidence optics have been used for other x-ray spectroscopy applications, notably in three other co-pending patent applications by this inventor (U.S. Application Nos. 543,170 and 797,199; and international application No. PCT/US96/16234, which was published as WO97/14156. However, the optics described herein, in contrast to the earlier disclosures, are not necessarily collimators or focusers but can simply be described as flux concentrators, although more accurately they act as flux preservers.

These optics 20 solve the problem of gathering emitted isotropic x-rays 14 that are diverging into a large angle guiding the redirected x-rays 18 through an aperture. This aperture is the surface of the detector 16, therefore, it is immaterial where the redirected x-rays 18 pass through the aperture. Because the redirected x-ray flux merely has to pass through the detector aperture and it is not necessary that it be in the form of a parallel beam, the optic does not need to be a collimator. These optics 20 may, therefore, be very simple and their geometry and surface roughness requirements are less stringent, compared to presently available systems, thus making these collection optics inexpensive to produce. For visible light, the capture illustrated in FIG. 2 would be unremarkable, but for x-rays the fabrication of such reflecting optics has been so problematic that they have not been previously considered. It is the difficulty of fabricating x-ray optics which has kept others from considering such optics as applied herein, thus, most people believe that these x-ray optics are not practical.

In addition, these optics also solve the problem of limiting the area of the target sample 12 from which x-rays reach a detector 16. For example, in x-ray fluorescence, an incident energy beam 10 consisting of x-rays is used to irradiate a large area of the target sample 12. The sample will become excited by the incident x-rays and, in turn, emit isotropic x-rays 14 which are then read by a detector 16 and analytically characterized to provide sample identification. Most samples 12, however, are not homogeneous and will emit x-rays which vary in spectrum according to the molecular composition of each microlocality within the sample. By limiting the area of the target sample 12 seen by the detector, the redirected x-rays 18 may be characterized to yield spatial resolution of the composition of the target sample 12. Currently, this is accomplished by placing a small aperture very close to the x-ray emitting sample, so that only those x-rays passing through the aperture will reach the detector. However, the disadvantage of this approach is that most of the x-rays passing through the aperture do not reach the detector because of the distance between the aperture and the detector, rather, the x-rays scatter and only few reach the detector. The optics 20 described herein may be used in place of the aperture, not only to increase the x-ray flux reaching the detector but also to further narrow the area of target sample 12 seen by the detector, thereby. surpassing present methods by providing both increased x-ray flux and increased spatial resolution of the sample.

Figure 6:
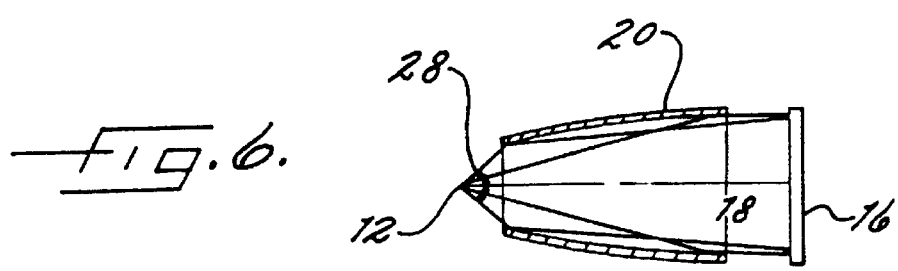
FIG. 6 shows an out of focus paraboloid optic used to concentrate diverging x-rays onto a detector in an energy dispersive x-ray spectrometer.

Several reflector shapes provide sufficient flux gain to be useful in various applications. The term "flux gain" is used herein to mean the increase in x-rays available to the detector 16 in an EDS instrument fitted with optic 20, as compared to an instrument without the optic. The flux concentrating optics 20 disclosed herein are figures of revolution, comprising sections such as cones, parabolas, hyperbolas, ellipsoids and others. Also effective as flux concentrating optics 20 are more complex figures of revolution embodying a plurality of any one shape or combining more than one shape in a single reflector, for example, composite reflectors comprising conical and/or paraboloidal and/or elliptical and/or hyperbolic reflecting surfaces in addition, for example, the optic could be fashioned as an out-of-focus paraboloid, FIG. 6, where the paraboloid focus 28 is essentially not coincident with the x-ray source. While all these reflector shapes are suitable as flux concentrating optics 20, the specific reflector geometry chosen for a particular application will depend on various considerations, including desired flux gain, source of the x-rays to be analyzed working distances, size of the aperture through which the x-rays must be guided, desired area of the x-ray emitting material to be covered, and others.

The optical fabrication process developed by this inventor and claimed for collimator construction in co-pending U.S. patent application No. 08/543,170, and co-pending international application No. PCT/US96/16234, incorporated herein by reference, is ideally suited for fabrication of flux concentrating optics 20. However, there are known in the art many other ways of fabricating these optics in addition to the method described in the above referenced patent application, including epoxy replication of molds, galvanoforming, controlled shaping of internal surfaces, bending of smooth sheets of material and others.

OPERATION OF THE INVENTION

Those skilled in the art will appreciate that this invention provides an improvement that was previously unavailable in energy dispersive x-ray spectrometry instrumentation. The operation of the invention is dependent upon reflectors 20 which collect a segment of the available flux of x-rays emitted 14 by a target sample 12 and redirects the x-rays 18 to the instrument's detector device 16.

Figure 3:
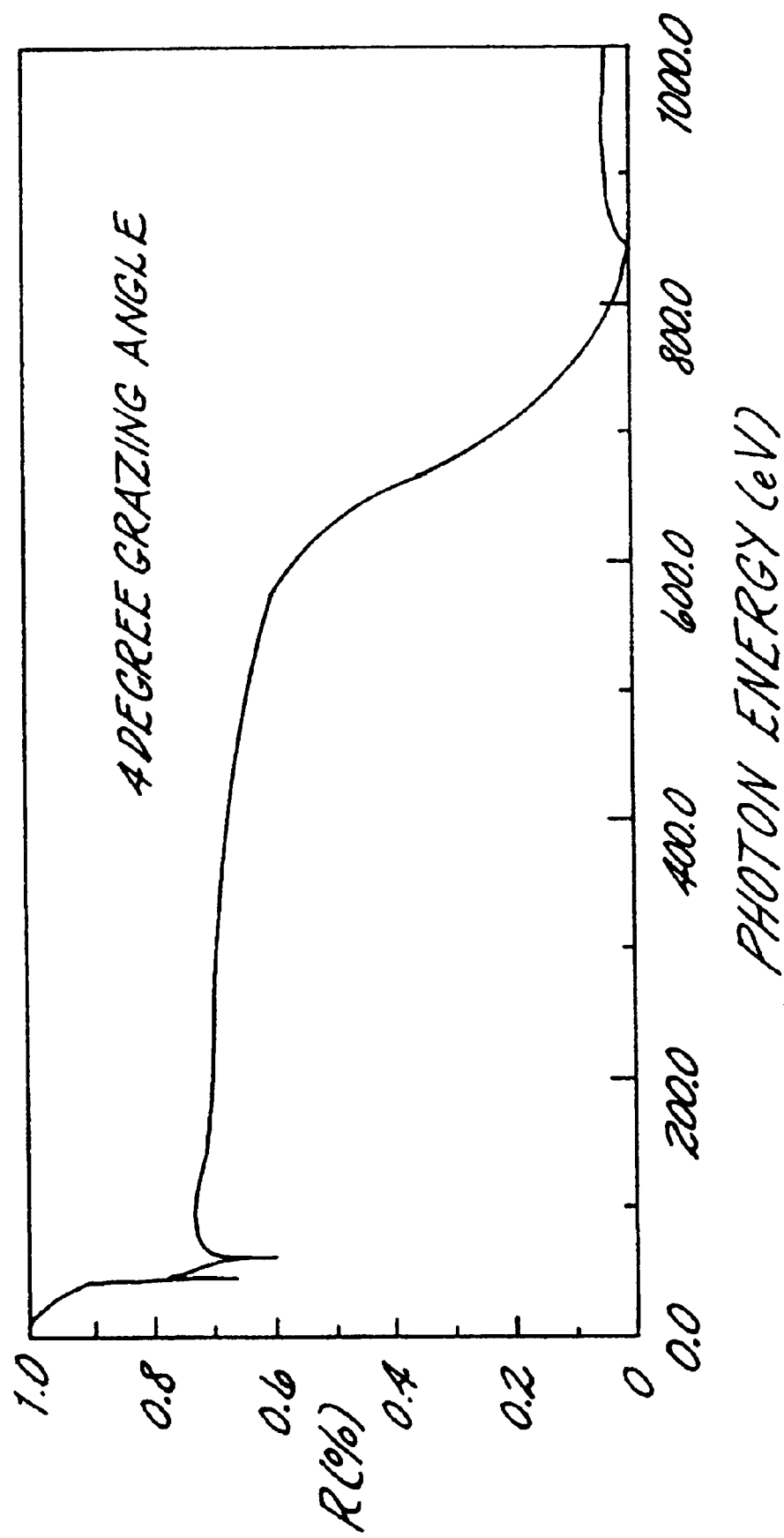
FIG. 3 is a graph of reflectivity as a function of photon energy for a nickel reflector.
Figure 4:
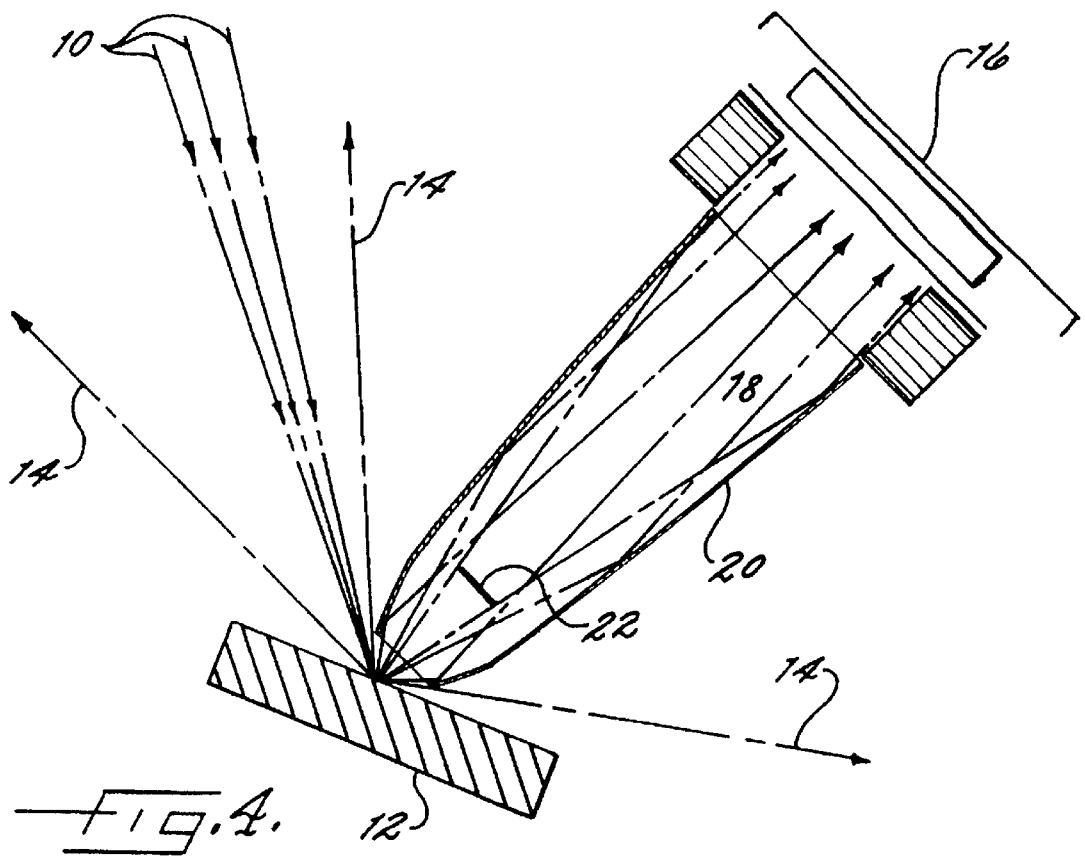
FIG. 4 illustrates one embodiment of the optic being used with an energy dispersive x-ray spectrometer to capture and guide the x-ray flux to the detector.
Figure 5:
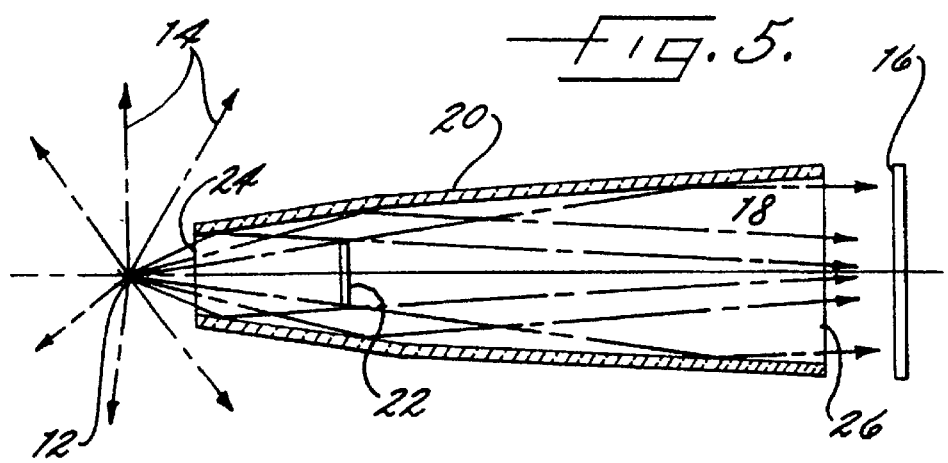
FIG. 5 shows a conical optic with a double taper being used to collect an x-ray flux to direct to a detector.

Grazing incidence optics reflect x-rays only for very small angles with respect to the reflecting surface (FIG. 3), and the reflectivity is a strongly decreasing function of grazing angle and x-ray energy. Reflectivity is also a strong function of the type of reflecting surface, a metal or metal alloy, and various surfaces may be chosen to match the x-rays of interest. In most grazing incidence x-ray optics, scatter from reflecting surfaces due to micro-roughness is a serious problem, but in this case it is less severe and can even be used to advantage. In most x-ray optical systems, the accuracy of the surface figure of the reflecting surface is critical in guiding the reflected x-rays in the desired direction but in this case, small variations will still allow the x-rays go through the detector, therefore making accuracy less important.

Figure 2:
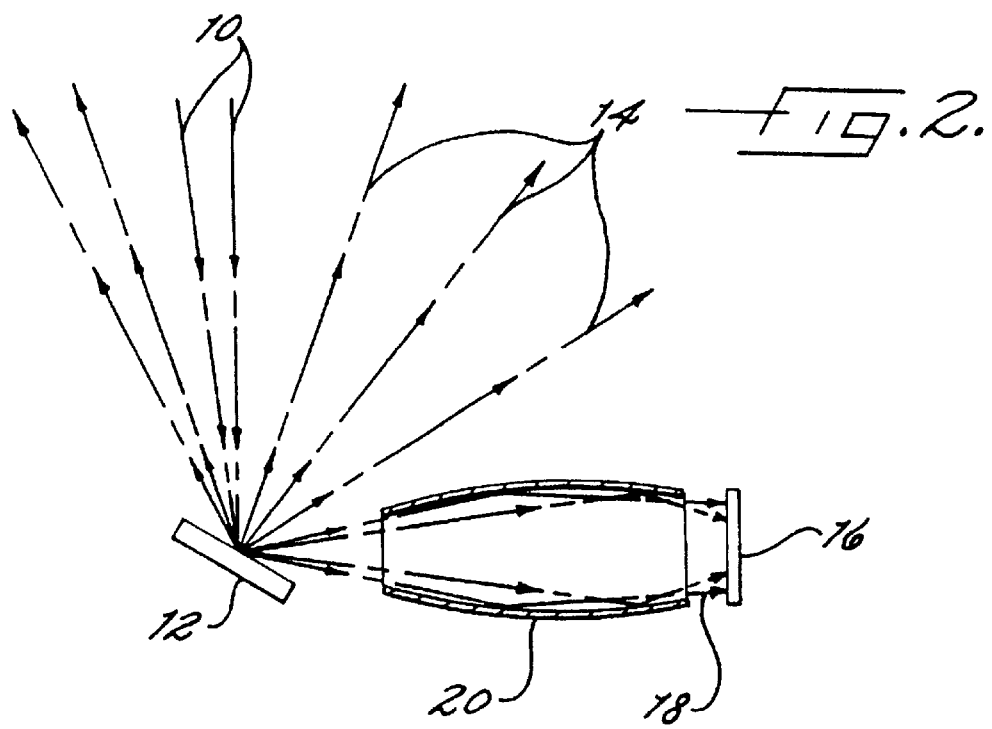
FIG. 2. shows the same detector with a flux concentrating optic of some type redirecting captured x-rays, which would otherwise be missed, onto the detector surface.

Referring to FIG. 2, with no losses on reflection the flux gain in an analytical instrument fitted with such an optic 20, relative to no optic, would be given by the formula $$G = I_o / I_d$$

where $I_d$ is the solid angle subtended by the detector and $I_o$ is the solid acceptance angle of the optic. If the angle subtended by the detector is small, a relatively small increase in effective acceptance angle, due to the acceptance angle of the optic, can give a large gain. Even where these optics produce a small gain, they may provide enough of an improvement in a particular analytical system to be considered significant.

Because of the strong decrease of reflectivity with increasing grazing angle, it is desirable to minimize the bend angle of an x-ray to make it go through the detector aperture. The minimum bend angle for an x-ray is the angle which makes it pass into the outer edge of the detector, although greater bend angles will work with reduced reflectivity. For cases where the bend angle is so large that it would result in unacceptably low reflectivity, multiple smaller bend angles may be used, taking advantage of the fact that sometimes several smaller reflections give better total reflectivity than a single large bend. This is particularly true for higher x-ray energies.

If the entrance aperture 24 of the optic is blocked by a stop 22, so that no direct x-rays reach the detector, only the lower energy reflected x-rays will reach it and the optic effectively becomes a low energy pass filter. The grazing angles and reflecting surface may be chosen specifically to determine the energy passed by such an optic. In addition, optics of this type effectively limit the accepted x-ray flux to that emitted from a small area so that, even if a large area is radiating, the user can be assured that the x-rays originate from a specific small area.

In summary, this invention teaches an improvement in energy dispersive x-ray spectrometry through the use of optics using the principle of total external reflection for delivering an increased flux of x-rays onto the detector. These flux concentrating optics are generally shaped as tubes having as longitudinal cross section a figure of revolution, such as cones, parabolas, hyperbolas, ellipsoids and others. Also disclosed as effective flux concentrating optics are more complex figures of revolution embodying a plurality of any one shape or combining more than one shape in a single reflector, for example, compound conical reflectors, compound parabolic reflectors, compound elliptical reflectors and compound hyperbolic reflectors, as well as off-axis and out-of-focus figures of revolution. These optics may also be used as low energy pass filters. The reflecting surface of the flux concentrator optic may be selected from the group of metals and their alloys, the choice made to optimize the optic's performance. The improved EDS may be incorporated in instruments having other applications, including transmission electron microscopy, scanning electron microscopy, electron microprobes, x-ray fluorescence instrumentation, and may also be used for inspection of semiconductor vias. The improved EDS also provides increased spatial resolution of the sample, as described herein above.

What is claimed is:

1. An energy dispersive x-ray spectrometer comprising:
    a) a beam source generating a beam of exciting energy directed at a target to thereby cause said target to emit x-rays;
    b) a reflector for reflecting said emitted x-rays, said reflector having a reflector body generally shaped in the form of a tube having an inner cavity, an entrance aperture positioned for providing an entrance opening into said inner cavity, an exit aperture positioned for providing an exit opening from said inner cavity, said inner cavity comprising a seamless surface of x-ray reflective material for reflecting said emitted x-rays, said reflector positioned substantially adjacent said target to collect emitted x-rays through the entrance aperture and reflect said x-rays from the x-ray reflecting surface through the exit aperture; and
    c) a detector having a detector aperture positioned adjacent the exit aperture of said reflector for detecting reflected x-rays to thereby generate data corresponding to said x-rays.

2. The energy dispersive x-ray spectrometer of claim 1, wherein said reflector includes an entrance aperture having an area smaller than said target to thereby collect x-rays emitted by generally only a predetermined area of said target.

3. The energy dispersive x-ray spectrometer of claim 1, wherein said x-ray reflecting surface further comprises at least one predetermined x-ray reflective material selected from metals and metal alloys.

4. The energy dispersive x-ray spectrometer of claim 1, wherein said reflector further comprises a shape of at least one figure of revolution.

5. The energy dispersive x-ray spectrometer of claim 1, exciting energy comprises substantially parallel x-rays.

6. The energy dispersive x-ray spectrometer of claim 1, further comprising a stop positioned relative to said reflector so as to thereby allow generally only reflected x-rays to pass through the exit aperture.

7. The energy dispersive x-ray spectrometer of claim 1, wherein said beam of exciting energy comprises energy selected from electrons, and x-rays.

8. A method for energy dispersive x-ray spectrometry, the method comprising the steps of:
    a) irradiating a target with a beam of exciting energy sufficiently to thereby cause the target to emit x-rays;
    b) collecting emitted x-rays in a reflector having a reflector body generally shaped as a tube having a first end and a second end, an inner cavity positioned between the first end and the second end, an entrance aperture positioned generally at the first end to connect with the inner cavity thereby providing an entrance opening into the inner cavity, an exit aperture positioned generally at the second end to connect with the inner cavity thereby providing an exit opening from the inner cavity, a seamless x-ray reflecting surface for reflecting the x-rays, the reflector positioned adjacent the target to collect the emitted x-rays through the entrance aperture and receive the emitted x-rays on the x-ray reflecting surface to thereby reflect the x-rays through the exit aperture; and
    c) detecting the reflected x-rays in a detector having a detector aperture positioned adjacent the exit aperture of the reflector for collecting substantially all said reflected x-rays.

9. The method of claim 8, wherein collecting comprises emitted x-rays from substantially a predetermined area of said target.

10. The method of claim 8, wherein the beam of exciting energy comprises energy selected from electrons, x-rays, and substantially parallel x-rays.

11. The method of claim 8, wherein the collecting further comprises allowing generally only reflected x-rays to pass through the exit aperture.

12. The method of claim 8, wherein the x-ray reflecting surface further comprises a shape of at least one figure of revolution.

13. The method of claim 8, wherein the x-ray reflecting surface further comprises at least one predetermined x-ray reflective material selected from metals and metal alloys.

14. An energy dispersive x-ray spectrometer comprising:
    a) a source of incident x-rays;
    b) a target receiving said incident x-rays so as to generate emitted x-rays from said target responsive to said incident x-rays;
    c) a detector for receiving and quantifying x-rays emitted by said target; and
    d) a reflector generally shaped as a tube having an entrance aperture and an exit aperture, said reflector further comprising an x-ray reflecting seamless surface shaped as a figure of revolution for reflecting x-rays by grazing incidence, said reflector being positioned sufficiently close to said target to collect said emitted x-rays through said entrance aperture and receive said emitted x-rays on said reflecting surface, thereby to reflect and to discharge said emitted x-rays from said exit aperture, whereby said emitted x-rays are redirected onto the detector.

15. The energy dispersive x-ray spectrometer of claim 14, wherein said reflecting surface further comprises a predetermined material selected from the group consisting of metals and metal alloys.

16. The energy dispersive x-ray spectrometer of claim 15, wherein the shape of said reflecting surface further comprises a plurality of figures of revolution.

17. The energy dispersive x-ray spectrometer of claim 16, wherein said reflector further comprises a stop at said entrance aperture.

18. The energy dispersive x-ray spectrometer of claim 15, wherein said reflector further comprises a stop at said entrance aperture.

19. A method for improved energy dispersive x-ray spectrometry, said method comprising the steps of:

a) striking a target with a beam of incident x-rays;

b) emitting x-rays from the target in response to striking;

c) receiving the emitted x-rays in a reflector generally shaped as a tube having an entrance aperture and an exit aperture, the reflector further comprising an x-ray reflective seamless surface shaped as a figure of revolution for reflecting the emitted x-rays by grazing incidence, the reflector being positioned sufficiently close to the target to receive a substantial fraction of the emitted x-rays through the entrance aperture; and d) reflecting the emitted x-rays from the x-ray reflective surface such that the emitted x-rays thereby emerge from the exit aperture redirected onto a detector.

20. The method of claim 19, wherein said reflecting surface further comprises a predetermined material selected from the group consisting of metals and metal alloys.

21. The method of claim 20, wherein the shape of said reflecting surface further comprises a plurality of figures of revolution.

22. The method of claim 21, wherein said reflector further comprises a stop at said entrance aperture.

23. The method of claim 20, wherein said reflector further comprises a stop at said entrance aperture.

24. A method for energy dispersive x-ray spectrometry, the method comprising the steps of:

irradiating a target with energy so as to cause the target to emit x-rays; and reflecting the emitted x-rays along a seamless x-ray reflecting surface generally shaped as a tube to thereby convey the x-rays toward a detector for generating data corresponding to the x-rays.

25. The method of claim 24, wherein reflecting comprises at least one predetermined x-ray reflective material selected from metals and metal alloys.

26. The method of claim 24, wherein the reflecting surface comprises at least one figure of revolution.

27. The method of claim 24, wherein reflecting comprises blocking substantially all but reflected x-rays from passing through the x-ray reflector.

28. The method of claim 24, wherein irradiating comprises energy selected from electrons, and x-rays.

29. The method of claim 24, wherein irradiating includes energy comprising a beam of substantially parallel x-rays.

30. The method of claim 24, further comprising collecting x-rays emitted substantially from a predetermined area of the target.

31. An x-ray spectrometer comprising:

a source of x-rays;

an energy dispersive x-ray detector including a detector surface and a generally planar detector entrance aperture having an area larger than said source; and an optic including a seamless x-ray reflective surface having an optical axis of cylindrical symmetry, an entrance aperture, and an exit aperture to thereby provide within the optic total external reflection of the x-rays;

wherein the entrance aperture of said optic is positioned relative to said source so as to collect and reflect x-rays toward the detector entrance aperture along a plurality of angles of incidence relative to the generally planar detector entrance aperture so that substantially the entire generally planar detector entrance is illuminated by x-rays.

32. The x-ray spectrometer of claim 31, wherein said optic collects and reflects x-rays toward the detector entrance aperture along a plurality of divergent angles of incidence relative to the generally planar detector entrance aperture.

33. The x-ray spectrometer of claim 31, further comprising a stop positioned relative to said optic so as to allow generally only reflected x-rays to pass through the optic exit aperture.

34. The x-ray spectrometer of claim 31, wherein said optic further comprises a plurality of optics.

35. The x-ray spectrometer of claim 31, wherein said optic further comprises a plurality of optics arrayed along a common optical axis.

* * * * *